(12) United States Patent
Allen et al.

(10) Patent No.: US 7,527,820 B2
(45) Date of Patent: May 5, 2009

(54) COMPOSITION RESULTING FROM PROCESS FOR EXTRACTING CAROTENOIDS FROM FRUIT AND VEGETABLE PROCESSING WASTE

(75) Inventors: Stephen D. Allen, Eagle, ID (US); Michael R. Rusnack, Star, ID (US)

(73) Assignee: Water Solutions, Inc., Eagle, ID (US)

( * ) Notice: Subject to any disclaimer, the term of this patent is extended or adjusted under 35 U.S.C. 154(b) by 0 days.

(21) Appl. No.: 11/561,795

(22) Filed: Nov. 20, 2006

(65) Prior Publication Data

US 2007/0071861 A1    Mar. 29, 2007

Related U.S. Application Data

(62) Division of application No. 10/706,498, filed on Nov. 12, 2003, now Pat. No. 7,138,152.

(60) Provisional application No. 60/425,426, filed on Nov. 12, 2002.

(51) Int. Cl.
*A23L 1/48* (2006.01)

(52) U.S. Cl. .................. 426/655; 426/429; 426/481; 426/430; 426/495; 426/648; 426/650

(58) Field of Classification Search ............... 426/429, 426/481, 430, 495, 648, 650, 655
See application file for complete search history.

(56) References Cited

U.S. PATENT DOCUMENTS

| | | | |
|---|---|---|---|
| 3,930,037 A | 12/1975 | Yokoyama et al. | |
| 3,998,753 A * | 12/1976 | Antoshkiw et al. ............ | 516/58 |
| 4,012,531 A | 3/1977 | Viani | |
| 4,851,339 A | 7/1989 | Hills | |
| 4,996,069 A | 2/1991 | de Hey et al. | |
| 5,245,095 A | 9/1993 | Graves et al. | |
| 5,510,551 A | 4/1996 | Graves et al. | |
| 5,648,564 A | 7/1997 | Ausich et al. | |
| 5,871,574 A | 2/1999 | Kawaragi et al. | |
| 5,897,866 A * | 4/1999 | Bombardelli et al. ....... | 424/777 |
| 6,265,593 B1 | 7/2001 | Best et al. | |
| 6,287,346 B1 | 9/2001 | Ofosu-Asante et al. | |
| 6,309,677 B1 | 10/2001 | Gorenbein et al. | |
| 6,326,504 B1 | 12/2001 | Piquer et al. | |
| 6,376,722 B1 | 4/2002 | Sanz et al. | |
| 6,407,306 B1 | 6/2002 | Peter et al. | |
| 2003/0180435 A1 | 9/2003 | Shi | |

FOREIGN PATENT DOCUMENTS

| | | |
|---|---|---|
| JP | 363145367 A | 6/1988 |
| JP | 407242621 A | 9/1995 |
| JP | 8120187 | 5/1996 |

* cited by examiner

*Primary Examiner*—Anthony Weier
(74) *Attorney, Agent, or Firm*—Kirton & McConkie; Evan R. Witt

(57) ABSTRACT

A process of extracting carotenoids from a source of fruit or vegetable processing waste including the steps of: admixing the source, a first organic solvent and a surfactant to form a slurry, whereby surface tension in tissue cell structure of the source is decreased, enhancing penetration of the surfactant into the tissue cell structure so that the carotenoids and the surfactant may form a combination; treating the slurry with a second organic solvent which solubilizes the combination; separating the treated slurry into a liquid fraction and a solid fraction; and separating a first portion from the liquid fraction, the first portion including a solution of the second organic solvent and the combination.

20 Claims, 7 Drawing Sheets

COMPOSITION RESULTING FROM PROCESS FOR EXTRACTING CAROTENOIDS FROM FRUIT AND VEGETABLE PROCESSING WASTE

CROSS-REFERENCE TO RELATED APPLICATIONS

This application is a divisional of U.S. application Ser. No. 10/706,498, filed Nov. 12, 2003 now U.S. Pat. No. 7,138,152, which claims the benefit of U.S. Provisional Application Ser. No. 60/425,426, filed Nov. 12, 2002, which applications are incorporated by reference.

FIELD OF THE INVENTION

The present invention relates to a process for extracting carotenoids from fruits and vegetable and, more particularly, to a more efficient and effective process for extracting higher concentration and yield levels of biologically active carotenoids from fruit or vegetable sources.

BACKGROUND OF THE INVENTION

Carotenoids are lipids, i.e. fat soluble yellow to orange to red pigments, universally found in the photosynthetic tissue of higher plants, algae and photosynthetic bacteria. They are found spasmodically distributed in flowers, fruits, roots of higher plants and fungi and bacteria. Carotenoids are synthesized de novo in plants and can be found in animals, especially marine invertebrates tending to concentrate in the gonads, skin and feathers. All carotenoids found in animals are ultimately derived from plants or protistan (unicellular or acellular organisms) carotenoids, although interestingly enough, because of metabolic alteration of the carotenoids (pigments), some carotenoids found in animals are not present in plants or protista.

Carotenoids are tetraterpenoids, consisting of eight (8) isoprenoid residues and can be regarded as being synthesized by the tail to tail dimerization of two (2) 20 carbon units each themselves produced by head to tail condensation of four (4) isoprenoid units. Hydrocarbon carotenoids are termed carotenes and oxygenated carotenoids are known as xanthophylls. Beta-carotene ($\beta$, $\beta$-Carotene) is probably the best known of the carotenoids. However, other carotenoids may include, but are not limited to, lycopene ($\psi$, $\psi$-Carotene, $C_{40}H_{56}$), lutein or xanthophylls ($\beta$, $\epsilon$-Carotene-3,3'-diol, $C_{40}H_{56}O_2$) and zeaxanthin ($\beta$, $\beta$-Carotene-3,3'-diol, $C_{40}H_{56}O_2$).

Other processes for extracting carotenoids from certain sources have been proposed. However, each has certain disadvantages and limitations. The most notable and common disadvantage of all prior art processes is the limited amount of carotenoids extracted from the source with respect to the total amount of carotenoids presenting the source, i.e. low yield and concentrations. Another major disadvantage in the instability of the extracted carotenoids which are susceptible to oxidation which further decreases their yield.

One prior art process describes a process for the formation, isolation and purification of comestible xanthophylls crystals from plants, namely lutein from marigold flower petals, zeaxanthin from wolf berries or capsanthin and capsorubin from red pepper. Such plant sources contain the xanthophylls in the esterified form as a mono- or di-C12-C18 long chain fatty acids such as lansic, myristic oleic, linolanic and palmitis acids, i.e. in the natural oils of the plant source.

This prior art process extracts the natural oils from the plant with hydrocarbon solvents, which are known to be toxic. This step includes repeated soaking of dried and ground marigold petals with warmed hexane for at least 8-10 hours. Next, the solvent must be removed so that only the natural oils containing the xanthophylls esters, i.e. oleoresin, remains.

The oleoresin is saponified by admixture with propylene glycol (1.2-propanediol) and an aqueous alkaline solution, preferably potassium hydrodroxide. The soaps generated by this saponification process attach to some of the carotenoids in the oleoresin as the mixture is heated under closely monitored temperatures for a considerable amount of time.

The saponification reaction cleaves the fatty acids, i.e. natural oils, from the xanthophylls diester, producing free xanthophylls in the form of crystals, as well as potassium soaps or sodium soaps of the fatty acids. Finally, the crystals are filtered and washed. The amount of xanthophylls extracted is approximately 6% by weight with approximately 80% natural oils.

Another prior art process describes methods to remove the natural oils in order to extract the carotenoids. This process attempts to extract hydrophobic compounds by admixing non-polar solvents, water-soluble organic solvents and a fruit or vegetable source for approximately 15-60 minutes. After admixing, the mass is forcibly centrifuged at 5000 rpm to draw of the supernatant for drying and further techniques to extract the carotenoid content. Again, the concentration and yield of the extracted carotenoids is quite low.

Still another prior art process describes the use of calcium analogs of various types to precipitate the carotenoids from the liquid phase of a slurry of all the components of the fruit or vegetable bring processed. Initially, a fruit or vegetable slurry is separated into a liquid fraction and a pulp fraction. Next, calcium analogs are added to precipitate the carotenoid from the liquid fraction. After precipitation, the carotenoid-enriched solids are separated from the carotenoid-depleted liquid fraction. The carotenoid-enriched solids may be utilized directly or may be further purified in order to separate the carotenoids from the other precipitated constituents. Further purification may include chemical and enzymatic hydrolysis and chemical and enzymatic degradation. As discussed above, the concentration and yield of the carotenoids are quite low and the carotenoid is present in a considerable amount of natural oil.

One disadvantage of the above methods is the low concentration and yield extraction levels for carotenoids from natural source. Another disadvantage is that the prior art processes have not been able to adequately dissociate the carotenoid from suspension in natural oils. Other disadvantages of these processes include time consuming and expensive steps necessary to generate an intermediate carotenoid-containing substance which each must be further manipulated in order to obtain a useful form of carotenoids. Accordingly, all known prior art processes are extremely time-consuming, ineffective, inefficient, costly to operate, involve multiple steps and cannot produce a near-pure carotenoid extraction in marketable quantities and concentrations.

Therefore, there exists a need in the art for a process which efficiently and effectively extracts high concentration and yield levels of biologically active, near-pure carotenoids in a stable form from fruit or vegetable sources, such as, but not limited to: 1) solids obtained from the waste treatment of the suspended solids present in the waste water from fruit or vegetable processing plants, 2) the pumice, or rough cut grinding of the exterior of the fruit or vegetable prior to processing of the fruit or vegetable, 3) fines and or slices of the fruit or vegetable present as a waste or as a disclaimed product, 4) any and all solids present from floor sweeping or general maintenance of the fruit or vegetable processing facility. There is also a need for such a simple, inexpensive, high-volume and manageable process that quickly penetrates the fruit or vegetable sources to extract higher yields of carotenoids that previously thought available all in a stable, transportable and useable form.

DETAILED DESCRIPTION OF THE INVENTION

Figure 1:
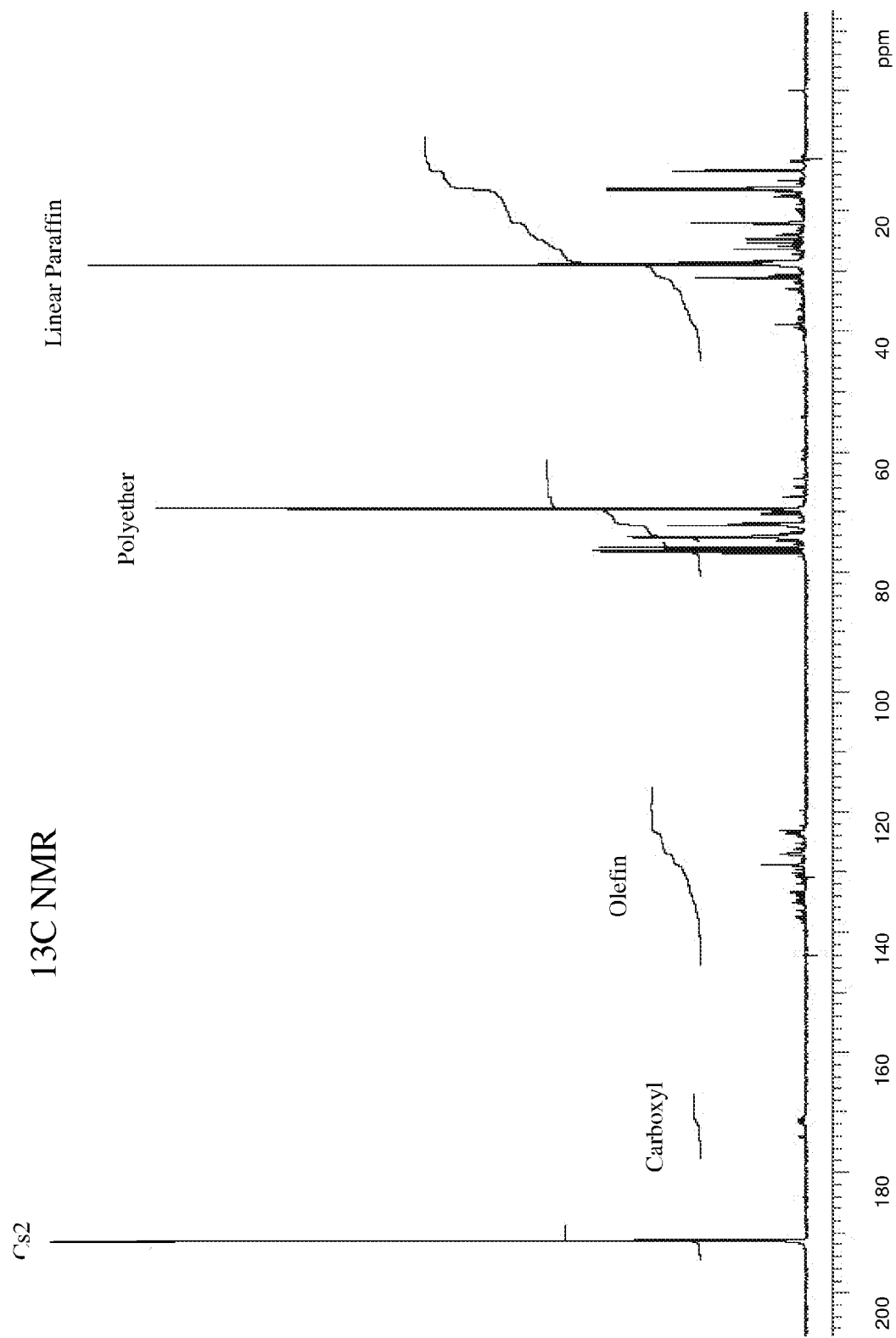
FIG. 1 is a NMR scan of a carotenoid sample obtained in accordance with the present invention.

According to the present invention, a process of extracting carotenoids from a source of fruit or vegetable processing waste includes the following steps: admixing the source, a first organic solvent and a surfactant to form a slurry, whereby surface tension in tissue cell structure of the source is decreased, enhancing penetration of the surfactant into the tissue cell structure so that the carotenoids and the surfactant may form a combination; treating the slurry with a second organic solvent which solubilizes the combination; separating the treated slurry into a liquid fraction and a solid fraction; and separating a first portion from the liquid fraction, the first portion including a solution of the second organic solvent and the combination.

The source of fruit or vegetable processing waste may include, but is not limited to tomatoes, leafy greens, such as but not limited to, kale, spinach, cress, parsley, beet greens, etc., and carrots. The source for the fruits and vegetables used in connection with the investigation set forth herein are often from high volume processing plants. Accordingly, it will be recognized that references to tomatoes will include not only tomatoes, but also rotted tomatoes, damaged tomatoes, tomato vines, tomato peels, rejected tomatoes, concentrated, high pH tomato peel, dry pumice and byproducts of a wastewater process. It will be further recognized that references to carrots will include not only carrots, but also rotted carrots, damaged carrots, carrot vines, carrot peels, rejected carrots, and byproduct of a wastewater process. Moreover, any and all leafy greens are compatible with the processes described and claimed herein. One of skill in the art will acknowledge that any other carotenoid-containing natural source may be successfully used in connection with the processes described and claimed herein. Use of the wording "source of fruit, vegetable, or fruit or vegetable processing waste" shall collectively refer to any and all of the possible above fruits and vegetables or any other suitable carotenoid-containing natural sources in any state of processing from whole fruit or vegetable to finished processing waste streams.

A process for extracting lycopene ($\psi$, $\psi$-Carotene) from a source of tomato processing waste includes the following steps: admixing the source, approximately 50-500 milliliters of ethanol for each kilogram of source and approximately 0.1-10 grams of surfactant for each kilogram of source, all to form a slurry; treating the slurry with carbon disulfide; separating the treated slurry into a liquid fraction and a solid fraction; and separating a first portion from the liquid fraction, the first portion including a solution of carbon disulfide, surfactant and lycopene.

A process for extracting zeaxanthin ($\beta$, $\beta$-Carotene-3,3'-diol) and lutein ($\beta$, $\epsilon$-Carotene-3, 3'-diol) from leafy greens includes the following steps: mincing the leafy greens; macerating the leafy greens with approximately 500 grams of distilled water for each kilogram of leafy greens; admixing the macerated leafy greens, approximately 50-500 grams of ethanol for each kilogram of leafy greens and approximately 0.1-10 grams of surfactant for each kilogram of leafy greens, all to form a slurry; treating the slurry with carbon disulfide; separating the treated slurry into a liquid fraction and a solid fraction; and separating a first portion from the liquid fraction, the first portion including a solution of the carbon disulfide, surfactant, zeaxanthin and lutein.

A process for extracting beta-carotene ($\beta$, $\beta$-Carotene) from a source of carrot processing waste includes the following steps: admixing the source, approximately 50-500 milliliters of ethanol for each kilogram of source and approximately 0.1-10 grams of surfactant for each kilogram of source, all to form a slurry; treating the slurry with carbon disulfide; separating the treated slurry into a liquid fraction and a solid fraction; and separating a first portion from the liquid fraction, the first portion including a solution of carbon disulfide, surfactant and beta-carotene.

A composition resulting from the above processes includes: a solution including, a combination composed of a surfactant and the carotenoids; and an organic solvent, wherein the combination is solubilized in the organic solvent at a concentration of approximately at least 0.44 milligrams/milliliter.

The source, as discussed above, is usually collected as a solid. For example, in connection with processing facilities the source of solid material includes, but is not limited to, solids from: the sorting table, the caustic peel process, dry pumice, rejected tomatoes and wastewater byproduct.

The sorting table or wet waste solids are from the sorter table plume. The fruits and vegetables are conveyed from the dump station to the process floor via plumes, i.e. small viaducts. The fruit or vegetable is sorted either to process or reject. The solid reject (rotted or damaged fruit or vegetable and vines) is collected, screened (water removed) and usually disposed of in a landfill.

The caustic peel process is used to remove the skin of the fruit or vegetable which is not desirable for processing. The skin is removed using a high pH solution of water and sodium hydroxide. The fruit or vegetable is sent for further processing and the peel material is usually sent to a high shear pump. The pH of the peel material is then lowered with citric acid and then is usually combined with the plant wastewater.

The dry pumice includes the seeds, peel and fruit or vegetable parts that are dried collected and usually disposed of.

It is not uncommon for an average of 700,000 pounds of fruits and vegetables to be received at the processing plant each hour. Each load is sampled and graded in real time. In the event the truckload is rejected, the fruit and vegetables are usually disposed of.

A solid generated by the process described and claim in U.S. patent application Ser. No. 10/706,168, titled "Extraction Methodology for Suspended and Dissolved Material from Fruit and Vegetable Wastewater", claiming priority from U.S. Provisional Patent Application No. 60/425,609, commonly owned by the Assignee hereof, which is incorporated by reference as if fully set forth herein, includes approximately 20-25% solids. This solid material is comprised of fruit or vegetable solids, peel and vine material which has been removed from the process wastewater. The solid material generated by this process has an oatmeal consistency.

In some embodiments of the present invention, the source of fruit and vegetable processing waste is minced prior to the admixing step. As used herein "minced" and any variation thereof shall be interpreted to include any preparation or processing to the source used to enhance extraction of the carotenoids. For example, the source solids may be cut, chopped or blended. It is within the teachings of the present invention that any other suitable preparation of the source may be used to provide adequate consistency to the source. Usually, after this initial preparation, the source will have sufficient water content to facilitate the subject extraction process. It will be recognized by those of skill in the art that a consistency of the source approximate to a liquefied slurry would be acceptable.

In some embodiments of the present invention, the source will need to be macerated prior to the admixing step. For example, water is preferably added to the dry pumice in a ratio of water to dry pumice of 3:1, to the vines in a ratio of water to vines of 2:1 and to the leafy greens in an amount of 1500 grams of distilled water for each kilogram of leafy greens. As used herein, "macerated" and any variation thereof shall be interpreted to include any softening of the source solid by association with any liquid used to enhance extraction of the carotenoids. Preferably, distilled water is used. Further preparation or processing may be necessary in accordance with the step described above such that the source solid have an acceptable consistency to facilitate extraction of the carotenoids.

One step of one embodiment of the present invention includes admixing the source, a first organic solvent and a surfactant to form a slurry. Such admixing step decreases the surface tension in tissue cell structure of the source, thereby enhancing penetration of the surfactant into the tissue cell structure so that the carotenoids and the surfactant may form a combination, as discussed in more detail below. The collection of the above materials is preferably mixed for a desired period of time at a desired speed. It is within the teachings of the present invention that the desired period of time and the desired speed of mixing may be adjusted as necessary to enhance extraction of the carotenoids. Generally, the desired period of time for mixing in this step ranges from 1 to 12 hours. A preferable period of time for mixing in this step for efficient yet effective performance of the process of the present invention is approximately 2 hours. Generally, the desired speed for mixing ranges from 20 to 100 revolutions per minute ("rpm"). A preferable speed for mixing for efficient yet effective performance of the process of the present invention is approximately 60 rpm. It is important to observe the mixing of the slurry to ensure that the bits of the source are moving through a liquid fraction of the slurry because this facilitates interaction of the first organic solvent and surfactant with the source.

The first organic solvent is preferably an alcohol. It is within the teachings of the present invention that the first organic solvent may be selected from the group consisting of ethanol, methanol, n-propanol, i-propanol, n-butanol, i-butanol, s-butanol, n-amyl alcohol, i-amyl alcohol, cyclohexanol, n-octanol, ethanediol, and 1,2-propanediol. Preferably, approximately 50-500 milliliters of first organic solvent is admixed for each kilogram of source.

It will be recognized by those of skill in the art that surfactants are organic compounds consisting of two parts. One is a hydrophilic portion that renders the compound sufficiently soluble or dispersible in polar solvents. For example, but in no way limiting, one polar solvent may be water or any other suitable polar solvent. The other is a hydrophobic portion, usually including a long hydrocarbon chain. These two portions, combine hydrophilic (water loving) and hydrophobic (water hating), moieties to render a compound that is active at the surface and thus able to concentrate at the interface between a surfactant solution and the other phase, air, soils, textile, etc. Surfactants have an enormous ability to penetrate into solids. It has been observed that surfactant based additives may penetrate into crevices no larger than 0.05 microns dependent on dose. This is well below the accepted level of penetration of 0.4 microns for water and other such solvents.

In one embodiment of the present invention, the surfactant is a non-ionic surfactant. In another embodiment of the present invention, the surfactant is a linear surfactant. Preferably, the surfactant is linear alkyl surfactant. Generally, approximately 0.1-10 milliliters of surfactant is admixed for each kilogram of source. In one embodiment of the present invention, preferably, approximately 2 grams of surfactant is admixed for each kilogram of source.

An unexpected result of the admixing step of the present invention is that the surface tension in tissue cell structure of the source was sufficiently decreased to enhance penetration of the surfactant in the tissue cell structure. A further, and more important, unexpected result of the admixing step was that the carotenoids and the surfactant formed a combination. As used herein, "combination" or any variation thereof shall be interpreted to include a description of the relationship between the surfactant and carotenoid which is not clearly borne out by this investigation, but may be commonly expressed in conceptual terms by the ideas of binding, associating, joining, connecting, linking, uniting, compounding or any other suitable word or expression.

The exact relationship between the surfactant and the carotenoid cannot currently be expressed with scientific certainty. However, nuclear magnetic resonance ("NMR") imaging performed by Process NMR Associates, LLC, 87A Sand Pit Road, Danbury, Conn. 06810 on the composition of matter that results from the process of extracting carotenoids in accordance with the present invention clearly indicates in FIG. 1 that there is a relationship. A sample of the composition of matter having a concentration level of 15 milligrams/milliliter of carotenoid in solution with an organic solvent was analyzed. The process to produce such a concentrated sample will be described in more detail below.

The NMR analysis indicated the presence of the organic solvent, surfactant and carotenoid (lycopene in this sample). Analysis and evaluation of the surfactant, independent of the carotenoid, verified that the polyether observed in the NMR scan was the surfactant. Therefore, based on the NMR scan shown in FIG. 1, those of skill in the art recognize that the carotenoid and surfactant are combined in some manner. In fact, the carotenoid to surfactant ratio appears to be 2:1. During the course of this investigation and others in accordance with the embodiments of the present invention, the carotenoids were present in mole ratio to the surfactant approximately at 1.6-2.2:1. The organic solvent was masked in the NMR scan in FIG. 1 because it was known to be present.

One step of another embodiment of the present invention includes treating the slurry with a second organic solvent which solubilizes the combination. Generally, the second organic solvent is a polar organic solvent. In one embodiment, the second organic solvent is non-miscible in water. Preferably, the second organic solvent is carbon disulfide. Generally, approximately at least 200 grams of second organic solvent is used to treat each approximately 200-250 grams of slurry. It will be recognized by those of skill in the art that use of carbon disulfide to solubilize the combination is advantageous because carbon disulfide will permit higher concentrations of carotenoids per unit of volume. Concentrations of carotenoids of approximately at least 1.5 milligrams/milliliter may be achieved in accordance with the present invention without the application of heat or pressure to the second organic solvent.

The slurry is preferably mixed for a desired period of time at a desired speed during the treating step. It is within the teachings of the present invention that the desired period of time and the desired speed of mixing may be adjusted as necessary to enhance extraction of the carotenoids. Generally, the desired period of time for mixing in this step ranges from 5 to 60 minutes. A preferable period of time of mixing for this step for efficient yet effective performance of the process of the present invention is approximately 20 minutes. Generally, the desired speed for mixing ranges from 20 to 100 rpm. A preferable speed for mixing for efficient yet effective performance of the process of the present invention is approximately 60 rpm. Again, it is important to observe the mixing of the slurry during this treating step to ensure that the bits of the source are moving through the liquid fraction of the slurry because this facilitates interaction of the second organic solvent with the combination.

One step of another embodiment of the present invention includes separating the treated slurry into a liquid fraction and a solid fraction. Generally the liquid fraction may be separated from the treated slurry by mechanical means. For example, mechanical means, such as, but not limited to, a fine mesh strainer, a press or any other suitable apparatus or device useful for separating, may be used to separate the solid fraction of the treated slurry from the liquid fraction which is collected in another vessel. Preferably, a plurality of mechanical means are used sequentially to separate virtually all of the liquid fraction from the solid fraction. Thereafter, the solid fraction is properly disposed of.

One step of another embodiment of the present invention includes separating a first portion from the liquid fraction. The first portion includes a solution of the second organic solvent and the combination, i.e. carotenoid and surfactant. Generally, the first portion may be separated by any accepted method, apparatus or device. Preferably, the first portion may be separated from the liquid fraction by a separation funnel after the liquid fraction is allowed to stabilize. Distinct layers form in the liquid fraction. The lowest level of the liquid fraction in the funnel contains the first portion. The first portion is rich in color because of the presence of the carotenoid. For example, lycopene show as a deep red or burgundy color, leafy greens (zeaxanthin and lutein) show as a dark yellow-green color and beta-carotene shows as a golden orange color. The first portion is removed from the separation funnel in a conventionally accepted manner.

In the event that the slurry has a mass greater than 250 grams, it is within the teachings of the present invention to fraction the slurry into generally equal portions for sequential performing the treating and separating steps. For example, where 1 kilogram of source is admixed with preferred amounts of first organic and surfactant, the resultant slurry may be fractioned into a number of approximately equal 200-250 gram portions. It will be recognized by those of skill in the art that this example is presented only to more accurately describe and enable the present invention as it would function in a higher volume setting as opposed to a laboratory and is not limiting in any manner.

A first slurry fraction is treated with the second organic solvent. Then the first treated slurry fraction is separated into a first liquid fraction and a first solid fraction. A first portion is separated from the first liquid fraction and is added to the second slurry fraction together with a small additional amount of second organic solvent in order to treat the second slurry fraction. Then the second slurry fraction is separated into a second liquid fraction and a second solid fraction. A first portion is separated from the second liquid fraction and is added to the third slurry fraction. This sequence is repeated for each of the number of slurry fractions until all the source has been processed in accordance with the present invention.

The final first portion of the above process in accordance with one embodiment of the present invention is a composition of matter composed of a solution including, a combination composed of a surfactant and the carotenoids; and an organic solvent (generally, the second organic solvent in accordance with the above description, but any other suitable organic solvent may also be used). For example, in one embodiment of the present invention, the first portion includes a solution of carbon disulfide, surfactant and lycopene. In another embodiment of the present invention, the first portion includes a solution of carbon disulfide, surfactant, zeaxanthin and lutein. In yet another embodiment of the present invention, the first portion includes a solution of carbon disulfide, surfactant and beta-carotene.

The combination is solubilized in the organic solvent at a concentration of approximately at least 0.44 milligrams/milliliter. Generally, the concentration of carotenoids in combination solubilized in the organic solvent averaged at least 0.5 milligrams/milliliter. In several investigations, the concentration of carotenoids ranged from approximately 0.44 milligrams/milliliter to approximately 1.5 milligrams/milliliter. The carotenoids which are present in the composition of matter, i.e. first portion, are approximately at least 95% trans and approximately less than 5% cis. Moreover, the carotenoids are present in the first portion in mole ratio to the surfactant approximately 1.6-2.2:1 as noted from the NMR scans. Finally, the carotenoids are present in the first portion at a yield of approximately at least 32 milligrams/kilogram. It will be recognized by those of skill in the art that the above process for extracting carotenoids from fruit and vegetable sources in accordance with the present invention is particularly advantageous in that it produces an extraordinary high yield of near-pure, biologically active carotenoids.

The first portion is also unexpectedly shelf stable over a wide temperature range and not affected by oxidation or ultraviolet light degradation. In other words, the composition of matter, i.e. first portion, is stable at standard temperature and pressure (0° C. and 1 atmosphere), stable at increased or decreased temperatures and pressures, stable under ultraviolet light exposure and resistant to oxidation. For example, universally recognized carotenoid standards, such as from Sigma-Aldrich of 3050 Spruce Street, St. Louis, Mo. 63103 or Chromadex of 2952 South Daimler Street, Santa Ana, Calif. 92705, usually degrade from a 100% pure sample, when it leaves the supplier, to a 55% pure sample, when received by the testing laboratory. This degradation of the standard carotenoids occurs despite proper handling of the material.

However, the composition of matter, i.e. first portion, did not show any measurable degradation when evaluated by the testing laboratory. These advantageous characteristics are attributed to the fact that the surfactant combines with the carotenoid as observed by the results of the NMR scan set forth above. Based on these observations, the hydrophobic end of the surfactant is combining with the carotenoid leaving the hydrophilic end free. This combination of the surfactant and carotenoid in the above manner indicates the rationale for the exceptional characteristics observed above. It will be recognized by those of skill in the art that the stability of this composition is particularly advantageous in that the yields and concentrations of the carotenoids do not materially change over the course of time.

The composition of matter, i.e. first portion, further includes oil from the source present in the solution at approximately less than 75 percent by weight. Generally, in accordance with the present invention, the oil from the source is present in the solution at approximately less than 15 percent by weight. Preferably, the oil from the source is present in the solution at approximately less that 5 percent by weight. The carotenoids are present in the composition are generally present in the solution at approximately more than 10 percent by weight. Preferably, the carotenoids are present in the solution at approximately at least 90 percent by weight. It will be recognized by those of skill in the art that the preferable concentrations of oil and carotenoids differ significantly from the prior art.

One step in another embodiment of the present invention includes collecting the carotenoid, i.e. lycopene, zeaxanthin, lutein, beta-carotene or other suitable carotenoids, from the first portion. Collecting the carotenoids includes the steps of: concentrating the carotenoids present in the first portion to a desired level; treating the concentrated first portion with a mixture to precipitate the carotenoids in crystalline form; and separating the crystalline carotenoids from the treated first portion.

The concentrating step is performed to maximize the solubility of the carotenoid in the second organic solvent, i.e. preferably carbon disulfide or other suitable polar solvent. It was commonly accepted in the prior art that the limit of solubility of carbon disulfide, the preferred second organic solvent, was 20 milligrams/milliliter. However, the investigations herein will show that the presence of the surfactant/carotenoid combination has adjusted the previously thought theoretical solubility limit.

In one embodiment, the step of concentrating increases the desired concentration level of the carotenoids to approximately greater than 0.44 milligrams/milliliter. Preferably, the desired concentration level of the carotenoids is in the range of 15-30 milligrams/milliliter. The step of concentrating may be performed by distillation or any other suitable process, apparatus or device useful for increasing the concentration of the carotenoids in the first portion. Temperature during the concentrating step is at a low temperature. Preferably, the low temperature is approximately less than 51° C. A number of conventional precipitation methods and processes were attempted. However, all failed. Yet another unexpected characteristic of the first portion is that the combination of the surfactant and carotenoid appears to have affected the ability of the carotenoid to be crystallized. Continued investigation led to the determination that the combination between the surfactant and carotenoid must be removed in order to crystallize the carotenoids.

The treating step in accordance with one embodiment of the present invention admixes a mixture and the concentrated first portion. The mixture generally includes ethanol and citric acid. Preferably, the citric acid is trisodium citrate. In one embodiment of the present invention, the mixture includes approximately 100 milliliters of ethanol and approximately 50 milligrams of citric acid for each 10 milliliters of concentrated first portion. The concentrated first portion treated with the mixture is agitated and the temperature thereof is adjusted as desired. Preferably, the concentrated first portion is maintained at approximately 47-50° C. during the step of treating the concentrated first portion. Time for the treating step may be adjusted as desired to balance maximum effectiveness and efficiency. Preferably, the time for the treating step is approximately 1 to 30 minutes. Subsequently, the treated first portion is allowed to settle into separate layers with the crystalline carotenoids at the bottom. The time for settling may be adjusted or varied as desired to maximize the extracted carotenoids and the efficiency of the process. In one embodiment, the treated first portion is allowed to settle overnight at a relatively low temperature. For example, typical refrigerator storage will be recognized by those of skill in the art as a satisfactory low temperature.

The crystalline carotenoids are separated from the treated first portion by mechanical means, e.g. any similar mechanical means as discussed above. Generally, the liquid fraction of the first portion is separated from the crystalline carotenoids by filter paper. The resultant liquid fraction is collected in a separate vessel for future re-use. Preferably, #4 Whatman filter paper is used.

One step in another embodiment of the present invention includes alternately washing the crystalline carotenoids with ethanol and distilled water for a desired number of cycles. Preferably, the ethanol is cool. It will be recognized by those of skill in the art that refrigerator storage temperature is acceptable. Subsequently, the crystalline carotenoids are allowed to dry. The washed and dried crystalline carotenoids are collected and stored in a closed vessel at a cool temperature. Conventional preservation steps, e.g. nitrogen blanket or any other suitable protective measure, must be taken at reduced temperatures because the crystalline carotenoids at this point are unprotected.

Figure 2:
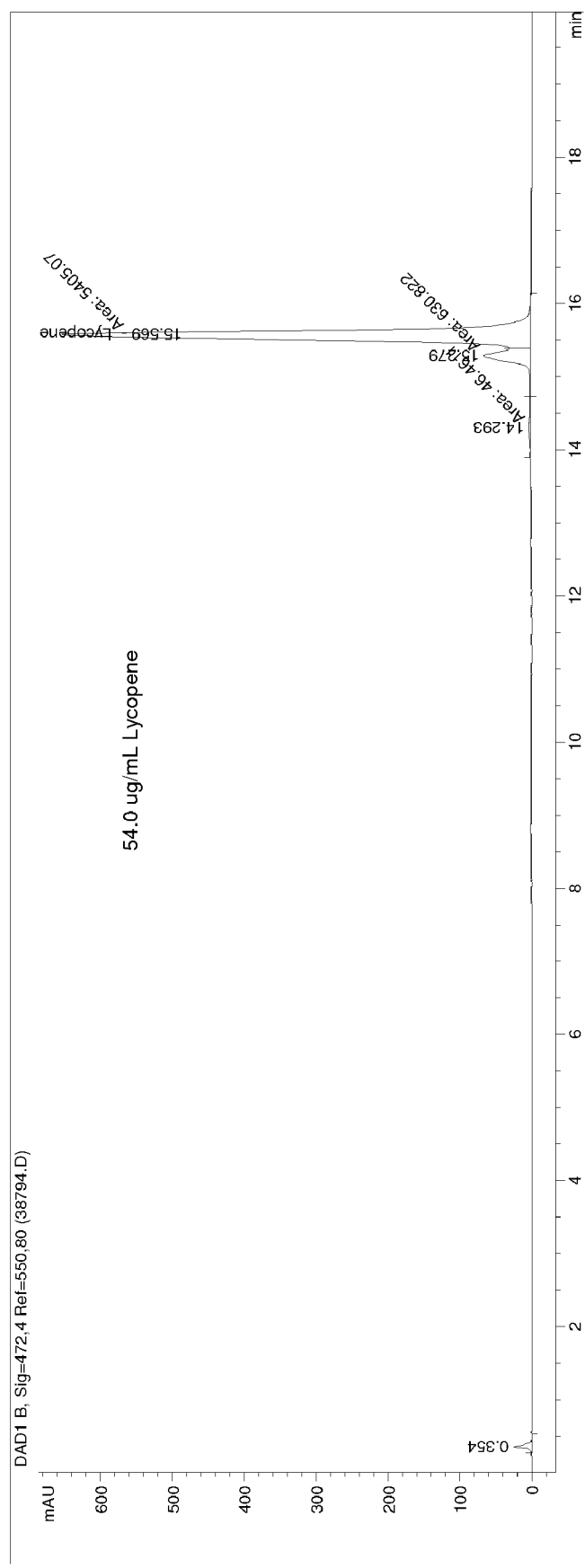
FIG. 2 is a HPLC scan of a known standard carotenoid (lycopene) at a concentration of 54 micrograms/milliliter.

The presence and purity of the crystalline carotenoids, i.e. lycopene, zeaxanthin, lutein, beta-carotene or any other suitable carotenoid, was verified through spectral analysis. The spectrum of the crystalline carotenoid was compared against the spectrum of a known standard referenced above. From this analysis, the effectiveness of the extraction process in accordance with the present invention is determined. An independent laboratory that specializes in the testing of carotenoids used Gas Chromatograph Mass Spectroscopy ("GC Mass Spec") and High Performance Liquid Chromatograph ("HPLC") to analyze the crystalline carotenoids obtained from the process in accordance with the present invention and the known standard. FIG. 2 sets forth a HPLC scan of a known standard carotenoid from one of the recognized sources, wherein the carotenoid, i.e. lycopene, is at a concentration of 54 micrograms/milliliter.

Figure 3:
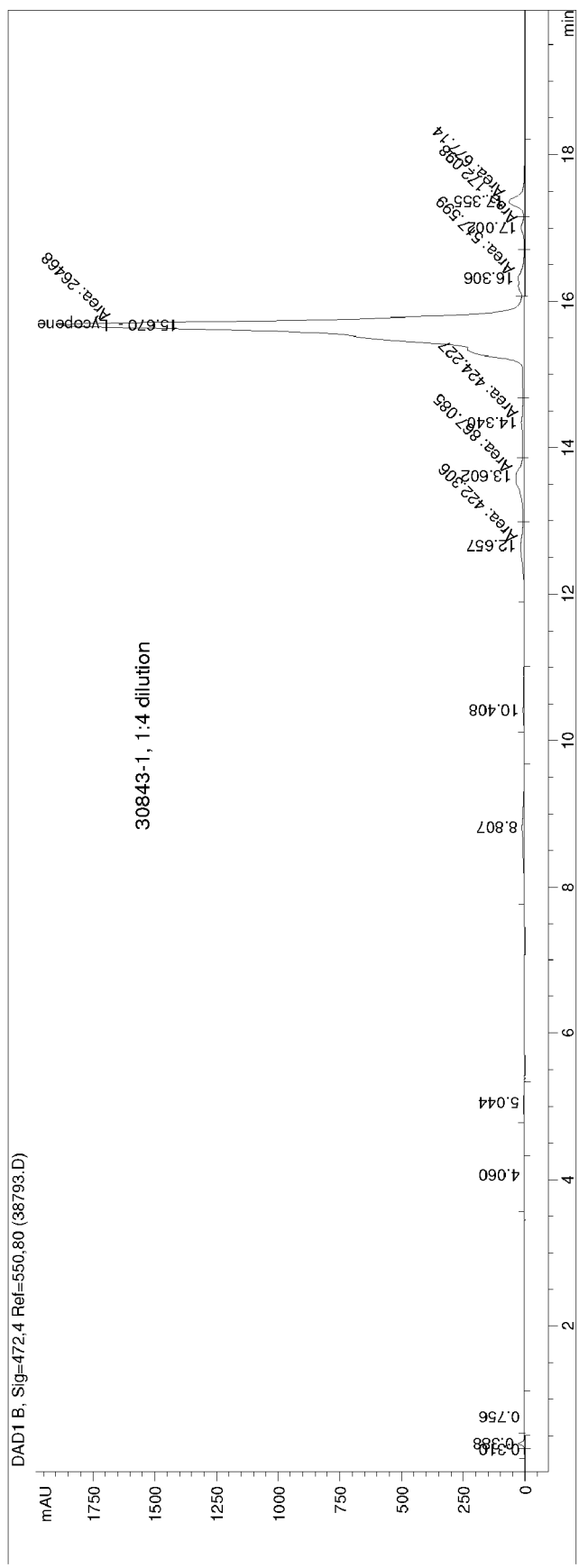
FIG. 3 is a HPLC scan of crystalline carotenoids processed within the scope of the invention at a 1:4 dilution.
Figure 4:
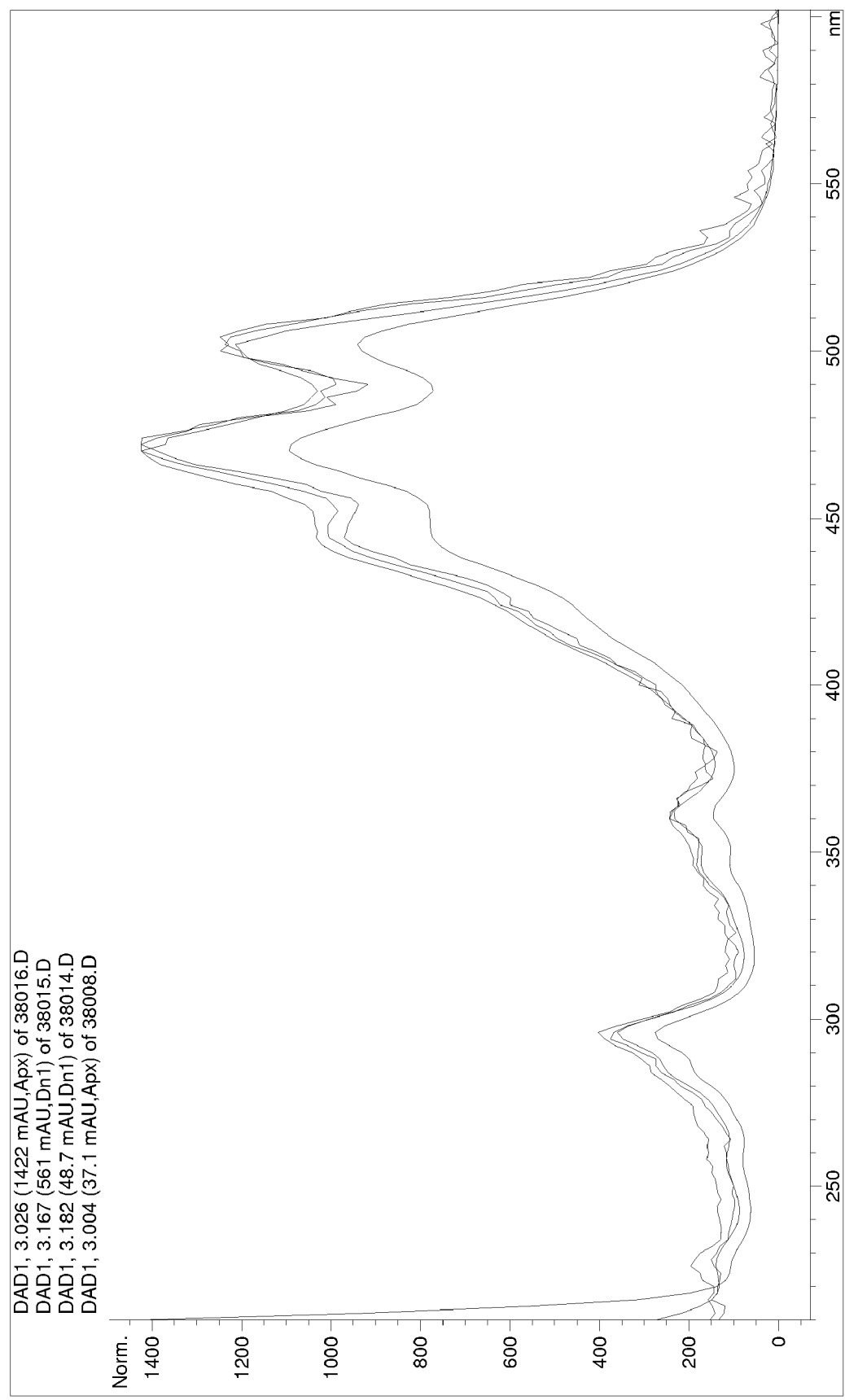
FIG. 4 is a HPLC scan of two crystalline carotenoids processed within the scope of the invention and two known carotenoid standards.

FIG. 3 sets forth a HPLC scan of the crystalline carotenoids processed in accordance with one embodiment of the present invention, wherein the carotenoids were diluted to a desired range FIG. 4 sets forth a HPLC scan of the two crystalline carotenoids processed in accordance with one embodiment of the present invention and two known carotenoid standards. It will be recognized by those of skill in the art that two crystalline carotenoids of the present invention are exceptionally pure in comparison to the two known standards.

From FIGS. 2-4, it is apparent that the extraction process in accordance with the present invention removes 2-8 times more carotenoids than were previously thought to be present in the source. For example, the lycopene content of tomatoes has been conventionally measured to be 3025 micrograms/100 grams of source. See JOURNAL OF FOOD COMPOSITION AND ANALYSIS 12, 169-196 (1999). Whereas the yield from the extraction process in accordance with one embodiment of the present invention is on the order of 8800 micrograms/100 grams of source (0.5 milligrams/milliliter concentration, 175 milliliters of first portion and 1000 grams of processed source).

EXAMPLE I

Lycopene

Figure 5:
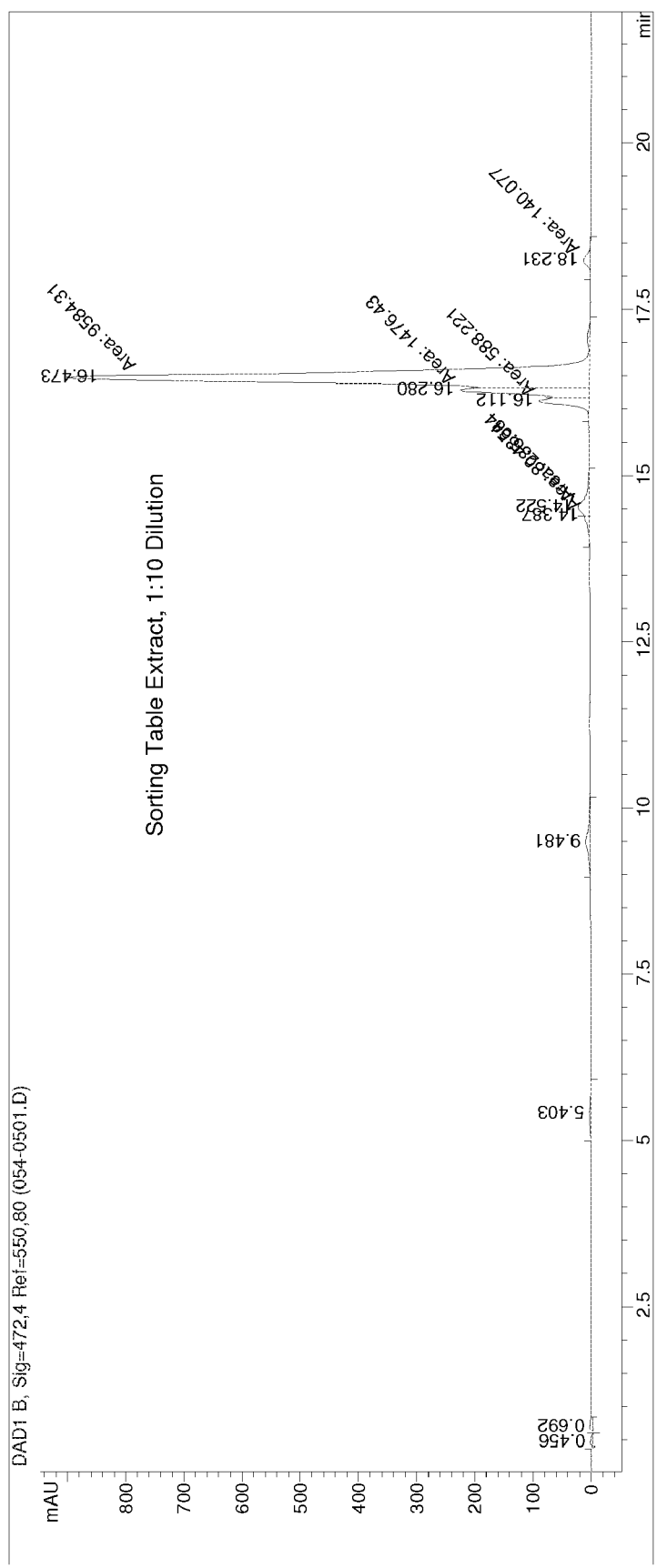
FIG. 5 is a HPLC scan of a carotenoid sample extracted from reject tomatoes processed within the scope of the invention.
Figure 6:
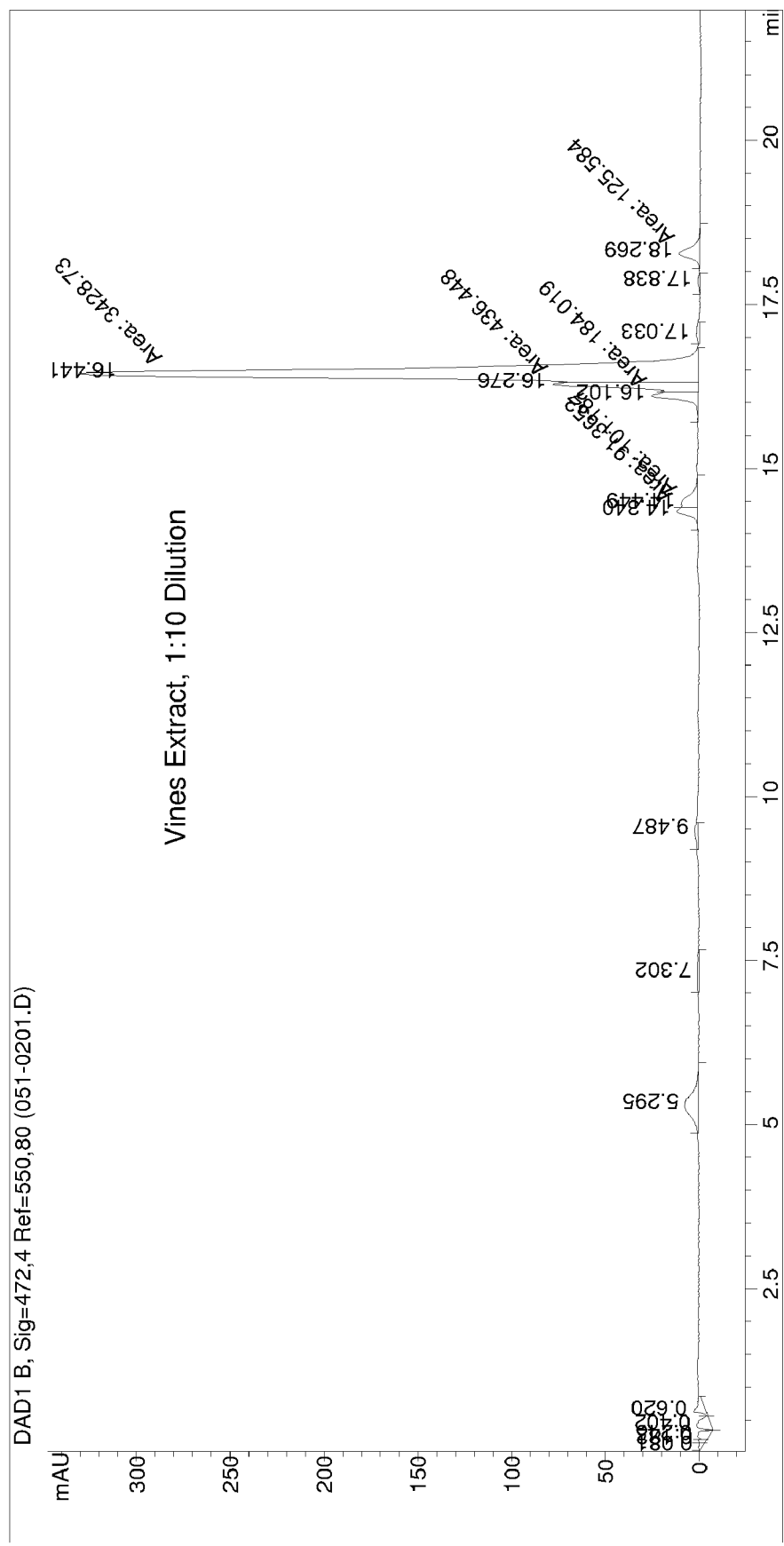
FIG. 6 is a HPLC scan of a carotenoid sample extracted from tomato vines processed within the scope of the invention.
Figure 7:
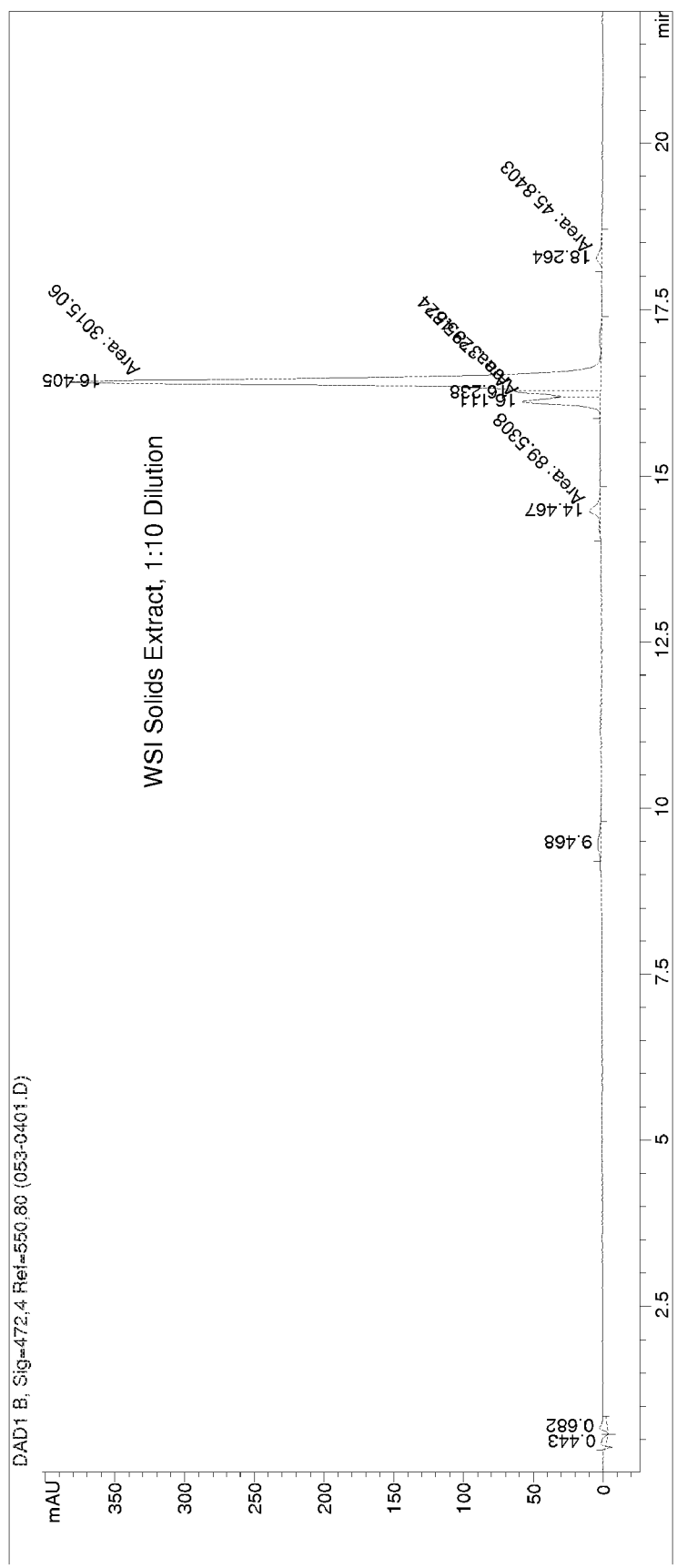
FIG. 7 is a HPLC scan of a carotenoid sample extracted from the wastewater byproduct solids within the scope of the invention.

Five samples were simultaneously tested. One kilogram of solids from the following were evaluated for the extraction of lycopene: sorter table (or wet waste), caustic peel, dry pumice, reject tomatoes, vines only and wastewater byproduct solids. All the solids were minced prior to the admixing step. Water was added to the dry pumice and the vines samples. Each sample was then admixed with 200 milliliters of ethanol and 2 grams of linear alkyl ethoxylate (Olin SLF-18) continuously for 2 hours to form a slurry. The slurry was then divided into approximately equal 200 gram fractions and 200 milliliters of carbon disulfide was added to the first slurry fraction and mixed for 20 minutes. The first slurry fraction was separated into a liquid fraction and a solid fraction. Then a first portion was separated from the liquid fraction. The first portion includes a solution of carbon disulfide, linear alkyl ethoxylate and lycopene which is then added with some small additional amount of carbon disulfide to the second slurry fraction for likewise processing until all slurry fractions have been processed. The results of this investigation are set forth in FIGS. 5-7 and Table 1. FIG. 5 sets for the results with respect to the reject tomatoes. FIG. 6 sets for the results with respect to the vines only. FIG. 7 sets for the results with respect to the wastewater byproduct solids. Table 1 sets forth the results with respect to all above investigations in a different format.

TABLE 1

| Raw Material Source | Concentration mg/mL | Lycopene Yield 1 Kg Waste |
|---|---|---|
| Reject Tomatoes | 1.54 | 284.9 mg |
| Vines Only | 0.566 | 107.5 mg |
| Wastewater Byproduct Solids | 0.493 | 93.5 mg |
| Sorter Table | 1.54 | 269.5 mg |
| Dry Pumice | 0.63 | 110.3 mg |

EXAMPLE II

Zeaxanthin and Lutein

Fresh kale was processed using a food processor in two steps. The entire stem (2"-3") and leaf (12"-18") are processed. The first processing step chops the kale into ½" sections with a slicing blade in the food processor. The source was reprocessed using a chopping blade. The step results in a finely chopped material that is ready for further processing. The above steps are repeated until one kilogram of material is prepared for further processing and evaluation. The source was then admixed with 200 milliliters of ethanol, 500 grams of distilled water and 2 grams of linear alkyl ethoxylate (Olin SLF-18) continuously for 2 hours at a low speed (40-60 rpm) to form a slurry. The slurry was then divided into approximately equal 200 gram fractions and 200 milliliters of carbon disulfide was added to the first slurry fraction and mixed for 20 minutes at medium speed. The first slurry fraction was separated into a liquid fraction and a solid fraction. Then a first portion was separated from the liquid fraction. The first portion includes a solution of carbon disulfide, linear alkyl ethoxylate, zeaxanthin and lutein which is then added with some small additional amount of carbon disulfide to the second slurry fraction for likewise processing until all slurry fractions have been processed. The results of this investigation show that the zeaxanthin and lutein are present in the first portion at a concentration of at least approximately 0.44 milligrams/milliliter.

EXAMPLE III

Beta-Carotene

Fresh carrots were used in this investigation. As discussed above, carrots in various different conditions were used, for example, rejected carrots, sorter table carrots, vines, carrot peels, rotten carrots, etc. Approximately 35% of the exterior of the carrot is used in this investigation. Rather than separate investigations as performed in connection with the lycopene investigations, all various different carrot sources were incorporated together. The source was processed using a food processor as discussed above. This step results in a finely chopped material that is ready for further processing. The above steps are repeated until one kilogram of material is prepared for further processing and evaluation. The source was then admixed with 200 milliliters of ethanol, 500 grams of distilled water and 2 grams of linear alkyl ethoxylate (Olin SLF-18) continuously for 2 hours at a low speed (40-60 rpm) to form a slurry. The slurry was then divided into approximately equal 200 gram fractions and 200 milliliters of carbon disulfide was added to the first slurry fraction and mixed for 20 minutes at medium speed. The first slurry fraction was separated into a liquid fraction and a solid fraction. Then a first portion was separated from the liquid fraction. The first portion includes a solution of carbon disulfide, linear alkyl ethoxylate, and bets-carotene which is then added with some small additional amount of carbon disulfide to the second slurry fraction for likewise processing until all slurry fractions have been processed. The results of this investigation are set forth in Table 2.

TABLE 2

| Beta-Carotene | Concentration mg/ml |
|---|---|
| Beta-Carotene Extraction | 0.421 |

The invention is not limited to the particular details of the apparatus shown or described and other modifications and applications may be contemplated. One or more steps may be combined into a single step while a single step may be expanded into multiple steps. In addition, the order of the steps may be altered. Certain other changes may be made in the above-described apparatus without departing from the true spirit and scope of the invention herein involved. It is intended, therefore, that the subject matter of the above depiction shall be interpreted as illustrative and not any limiting sense.

The invention claimed is:

1. A composition resulting from a process of extracting carotenoids from a carotenoid source of fruit, vegetable, or fruit or vegetable processing waste, the composition comprising:
   the carotenoid source;
   a first organic solvent comprising an alcohol;
   a non-ionic surfactant that forms a combination with the carotenoids; and
   a second organic solvent, which is polar,
   wherein the combination is solubilized in the polar organic solvent.

2. The composition as recited in claim 1, wherein the surfactant is a linear alkyl ethoxylate.

3. The composition as recited in claim 1, wherein the polar organic solvent is carbon disulfide.

4. The composition as recited in claim 1, wherein the mole ratio of carotenoids to the surfactant in the combination is approximately at 1.6-2.2:1.

5. The composition as recited in claim 1, further including oil from the source present in the solution at approximately less than 5 percent by weight and the carotenoids present in the solution at approximately at least 90 percent by weight.

6. The composition as recited in claim 1, wherein the carotenoids are present in the solution at approximately more than 10 percent by weight.

7. The composition as recited in claim 1, wherein the solution is shelf stable over a wide temperature range and not affected by oxidation or ultraviolet light degradation.

8. The composition as recited in claim 1, wherein the carotenoids are present in the solution at a yield of approximately at least 32 milligrams/kilogram of the source of fruit, vegetable, and/or fruit or vegetable processing waste.

9. The composition as recited in claim 1, wherein the carotenoids are selected from lycopene ($\psi$, $\psi$-Carotene), zeaxanthin ($\beta$, $\beta$-Carotene-3,3'-diol), lutein ($\beta$, $\epsilon$-Carotene-3,3'-diol), beta-carotene ($\beta$, $\beta$-Carotene), and mixtures thereof.

10. The composition as recited in claim 1, wherein the carotenoids comprise lycopene ($\psi$, $\psi$-Carotene).

11. The composition as recited in claim 10, wherein the source is selected from tomatoes, rotted tomatoes, damaged tomatoes, tomato vines, tomato peels, rejected tomatoes, concentrated, high pH tomato peel, dry pumice and byproduct of a wastewater process.

12. The composition as recited in claim 10, wherein the extracted lycopene is approximately at least 95% trans and approximately less than 5% cis.

13. The composition as recited in claim 1, wherein the carotenoids comprise zeaxanthin ($\beta$, $\beta$-Carotene-3,3'-diol) and lutein ($\beta$, $\epsilon$-Carotene-3,3'-diol).

14. The composition as recited in claim 13, wherein the source is selected from minced leafy greens, wolf berries, and marigolds.

15. The composition as recited in claim 13, wherein the extracted zeaxanthin and lutein is approximately at least 95% trans and approximately less than 5% cis.

16. The composition as recited in claim 1, wherein the carotenoids comprise beta-carotene ($\beta$, $\beta$-Carotene).

17. The composition as recited in claim 16, wherein the source is selected from the group consisting of carrots, rotted carrots, damaged carrots, carrot vines, carrot peels, rejected carrots, carrot peel and byproduct of a wastewater process.

18. The composition as recited in claim 16, wherein the extracted beta-carotene is approximately at least 95% trans and approximately less than 5% cis.

19. A composition resulting from a process of extracting carotenoids from a source of fruit, vegetable, or fruit or vegetable processing waste comprising:
   a solution including, a combination composed of a non-ionic linear alkyl ethoxylate surfactant and the carotenoids, wherein the carotenoids are selected from lycopene ($\psi$, $\psi$-Carotene), zeaxanthin ($\beta$, $\beta$-Carotene-3,3'-diol), lutein ($\beta$, $\epsilon$-Carotene-3,3'-diol), beta-carotene ($\beta$, $\beta$-Carotene), and mixtures thereof; and
   a polar organic solvent, wherein the combination is solubilized in the polar organic solvent at a concentration of approximately at least 0.44 milligrams/milliliter, and wherein the extracted carotenoids are approximately at least 95% trans and approximately less than 5% cis.

20. The composition of claim 19, wherein the mole ratio of carotenoids to the surfactant in the combination is approximately at 1.6-2.2:1.

* * * * *